United States Patent [19]

Kaplan et al.

[11] Patent Number: 4,772,589
[45] Date of Patent: Sep. 20, 1988

[54] ETOPOSIDE SOLUTION IN NMP

[75] Inventors: Murray A. Kaplan, Syracuse; Robert K. Perrone, Liverpool; Joseph B. Bogardus, Manlius, all of N.Y.

[73] Assignee: Bristol-Myers, New York, N.Y.

[21] Appl. No.: 924,463

[22] Filed: Oct. 29, 1986

[51] Int. Cl.⁴ .......................... A61K 9/66; A61K 9/42; C07H 15/20; C07H 15/24
[52] U.S. Cl. ........................ 514/33; 514/25; 514/27; 536/18.1; 424/455
[58] Field of Search ................. 536/18.1; 514/25, 27, 514/33; 424/455

[56] References Cited

U.S. PATENT DOCUMENTS

| | | |
|---|---|---|
| 4,540,564 | 9/1985 | Bodor ................................ 424/9 |
| 4,547,567 | 10/1985 | Umezawa et al. .................. 536/18.1 |
| 4,701,327 | 10/1987 | Henmi et al. ...................... 424/455 |
| 4,713,246 | 12/1987 | Begum et al. ..................... 424/455 |
| 4,716,221 | 12/1987 | Umezawa et al. ................. 536/18.1 |

FOREIGN PATENT DOCUMENTS 0193287 9/1986 European Pat. Off. .
60-239414 11/1985 Japan .
60-239415 11/1985 Japan .

OTHER PUBLICATIONS

Physician's Desk Reference, 40th Ed., pp. 725-727.
D. J. Stewart, Cancer Treat Rep., 69:269-273, 1985.

*Primary Examiner*—Ronald W. Griffin
*Attorney, Agent, or Firm*—Mollie M. Yang

[57] ABSTRACT

A stable solution of etoposide in 1-methyl-2-pyrrolidinone is disclosed. The solution can be diluted with a parenteral vehicle to yield an infusion solution containing up to 10 mg/ml etoposide activity without rapid etoposide crystallization. Solutions having etoposide concentration of as high as 500 mg/ml can also be prepared and used to fill gelatin capsules.

10 Claims, No Drawings

ETOPOSIDE SOLUTION IN NMP

BACKGROUND OF THE INVENTION

1. Field of the Invention

The present invention relates to a stable solution of etoposide in 1-methyl-2-pyrrolidinone (henceforth referred to as NMP).

2. Description of the Prior Art

Etoposide is a semi-synthetic product derived from podophyllotoxin. The material is identified by the chemical name 4'-demethylepipodophyllotoxin-9-(4,6-O(R)-ethylidine-$\beta$-D-glucopyranoside). It is approved by the Federal Food and Drug Administration for use in the treatment of refractory testicular cancer and has been proposed for use in the treatment of small cell lung cancer.

Etoposide is currently being marketed under the tradename VePesid as an injection solution containing for each ml, 20 mg of etoposide activity. Before administration by slow intravenous infusion, the solution is diluted with either 0.9% NaCl for Injection, U.S.P. or 5% Dextrose for Injection, U.S.P. to give a final etoposide concentration of 0.2 to 0.4 mg/ml. The diluted solutions are stable for 96 and 48 hrs, respectively (Physician's Desk Reference, Medical Economics Co., 40th Ed., pp. 725-7). Dilution of the commercial formulation by 50 to 100 times requires a large volume of parenteral vehicle and results in prolonged period of drug administration which causes patient inconvenience and discomfort. It is, therefore, desirable to have an etoposide formulation which allows the preparation of an infusion solution of high final etoposide concentration and which is free of etoposide precipitate for a convenient period of time. Such an infusion solution can greatly reduce the time required for drug infusion and represents a benefit to the patients. Japanese Kokai Nos. J60239414 and J60239415 disclose etoposide preparations which are stable against discoloration. European Patent Application No. 193287 discloses etoposide solution containing a water-soluble cellulose ether derivative or polyvinylpyrrolidone.

Etoposide may also be given orally. However, it has been shown that when etoposide is given in a gelatin capsule, a dose twice as high as an IV dose should be given in order to achieve the equivalent blood level (Stewart, D.J., Cancer Treat Rep, 69:269-273, 1985). When a high oral dose is to be given in capsule dosage form, it is desirable to have a concentrated solution of etoposide. Such a concentrated solution will enable the preparation of capsules of smaller sizes thereby allowing for easier ingestion, it may also reduce the number of capsules to be swallowed. The currently marketed etoposide solution having 20 mg/ml etoposide activity may be too dilute for the preparation of a convenient capsule dosage form.

Accordingly, an object of the present invention is to provide a solution of etoposide which upon dilution with a conventional aqueous parenteral vehicle yields a stable solution having a high final etoposide concentration not previously attainable. A further object concerns a concentrated solution of etoposide suitable for encapsulation within a gelatin capsule.

SUMMARY OF THE INVENTION

One aspect of the present invention is concerned with a stable etoposide solution in NMP which upon dilution with a parenteral vehicle provides a final solution containing upto about 10 mg etoposide activity per ml, and which shows no precipitation of etoposide for a prolonged period of time after said dilution.

Another aspect of this invention relates to a concentrated solution of etoposide in NMP which is suitable as a filling solution for gelatin capsules.

DETAILED DESCRIPTION

Etoposide is only sparingly soluble in water, its solubility in water being about 0.1 mg/ml. Thus, in order to prepare a solution of etoposide, an organic solvent or a mixture of organic solvents must be used. The choice of a suitable organic solvent for preparing pharmaceutical dosage forms is further limited to those that have high physiological safety. The marketed etoposide product is contained in a multi-solvent system.

1-Methyl-2-pyrrolidinone is a relatively non-toxic chemical and has been used as a solvent for polymers, chlordane, DDT, sorbitol, sugars, and numerous other materials. It is miscible with water, ethanol, ether, chloroform, benzene, ethyl acetate, and carbon disulfide.

It has now been discovered that, surprisingly, a solution of etoposide in 1-methyl-2-pyrrolidinone can be diluted with a parenteral vehicle such as Water for Injection, U.S.P., 5% Dextrose for Injection, U.S.P., or 0.9% NaCl for Injection, U.S.P., to yield a final aqueous solution having an etoposide concentration of upto 10 mg/ml without rapid etoposide crystallization. The aqueous solution thus prepared shows no precipitation of etoposide for a prolonged period of time; this is in sharp contrast to the currently available commercial formulation which when diluted to an etoposide concentration of about 0.5 mg/ml to about 5 mg/ml causes etoposide to crystallize out of solution within a short time. Table I presents the crystallization utility times (time noted at onset of crystallization) for static aqueous dilutions of a formulation of the present invention (MP) as compared to that of the currently marketed formulation (VP). Table II compares the crystallization utility times for stirred, shaken, and static aqueous dilutions of MP and VP. The MP formulation contains for each ml of solution, 20 mg etoposide, 1 mg of citric acid monohydrate, and 1-methyl-2-pyrrolidinone, q.s. to 1 ml; the VP formulation contains for each ml of solution, 20 mg of etoposide, 2 mg of anhydrous citric acid, 30 mg of benzyl alcohol, 80 mg of polysorbate 80, 650 mg polyethylene glycol 300, and 30.5% V/V ethyl alchohol (0.305 ml). The data presented in both Tables I and II clearly demonstrate the greatly enhanced utility time for the etoposide solution of the present invention over that for the commercial etoposide product. NMP is an unique solvent for etoposide, as solutions of etoposide in many other commonly used pharmaceutical solvents, such as dimethylacetamide, dimethylformamide, ethanol, 2-pyrrolidinone, dimethylisosorbide, 1-ethyl-2-pyrrolidinone, 1-isopropyl-2-pyrrolidinone, propylene glycol, polyethylene glycol-300, behave as the VP formulation with respect to crystallization utility time, i.e. rapid deposit of etoposide crystals when diluted with water to 0.5–5 mg/ml.

Etoposide is suitably stable in NMP. No activity loss was noted for neat-MP for 2-weeks at 70° C., 4-weeks at 45° and 56° C., and 2-months at 37° C.

TABLE I

CRYSTALLIZATION UTILITY TIMES FOR AQUEOUS DILUTED MP and VP FORMULATIONS AT 22° C. (STATIC SOLUTIONS)

| Formulation | Diluent | Etoposide Concentrations mg/ml | | | |
|---|---|---|---|---|---|
| | | 5*2 | 2 | 1 | 0.5 |
| MP | Water | >192*1 | >192 | 120 | >192 |
| | 5% Dextrose | >192 | >192 | 120 | >192 |
| | 0.9% Na Cl | 120 | 120 | 120 | 192 |
| VP | Water | 1 | 2.5 | 2.5 | 22 |
| | 5% Dextrose | 1 | 2.5 | 2.5 | 22 |
| | 0.9% Na Cl | 1 | 1 | 2.5 | 12 |

*1Time in hours when crystallization of Etoposide is first noted. Tests were conducted in Type-I flint glass vials.
*2Diluted to 10 mg/ml with water, MP and VP do not crystallize for at least one week at 22° C.

TABLE II

CRYSTALLIZATION UTILITY TIMES*1 FOR AQUEOUS DILUTED MP AND VP FORMULATIONS STATIC, STIRRED*2 AND SHAKEN*3

| Formulation | Etoposide*4 Concentration in mg/ml | DILUENT | | | | | | | | | | | |
|---|---|---|---|---|---|---|---|---|---|---|---|---|---|
| | | Water | | | | 0.9% Saline | | | | 5% Dextrose | | | |
| | | 4° C. Static | 22° C. Static | 22° C. Shake | 22° C. Stir | 4° C. Static | 22° C. Static | 22° C. Shake | 22° C. Stir | 4° C. Static | 22° C. Static | 22° C. Shake | 22° C. Stir |
| MP | 5*4 | >24–184 | >24–184 | >24–168 | >24–184 | — | — | — | — | — | — | — | — |
| | 2 | >24–184 | >24–184 | >32–96 | >24–48 | >144 | — | >168 | 120–168 | >144 | — | >168 | >168 |
| | 1*5 | >24–184 | >24–184 | >24–168 | >24–112 | >144 | — | >168 | >168 | >144 | — | >168 | >168 |
| | 0.5 | >24–184 | >24–184 | >24–168 | >24–184 | — | — | — | — | — | — | — | — |
| VP | 1 | 0.5 | 0.5 | 0.5 | 0.75 | <1 | <1 | <1 | 0.5 | <1 | <1 | <1 | 0.75 |

*1Utility time = time in hours when crystallization of Etoposide first noted.
*2Stirrer-bar stirred at approximately 120 R.P.M. in 10 cc Type-I flint glass vials.
*3Horizontal shaking at approximately 90 cycles/minute.
*4Diluted to 10 mg/ml with water, MP and VP do not crystallize for at least 1 week at 22° C.
*5MP diluted to 1 mg/ml of etoposide in water, normal saline solution or 5% dextrose remained clear and showed no activity losses for 48 hrs. at 4 and 24° C.

Additionally, etoposide exhibits an unexpectedly high solubility in NMP; its solubility in NMP being >500 mg/ml. The high etoposide concentration achievable renders the solution useful as gelatin capsule fill. Table III compares the solubility of etoposide in various solvents.

TABLE III

| Solvent | Etoposide Solubility mg/ml |
|---|---|
| Ethanol | <1.0 |
| Benzyl Alcohol | 104 |
| Propylene Glycol | 11 |
| Water | 0.1 |
| Dimethylisosorbide | 320 |
| 1-Methyl-2-pyrrolidinone | >500 |

The amount of etoposide contained in the solution of this invention is not specifically restricted but may be any amount convenient for pharmaceutical purposes. A preferred embodiment of the present parenteral solution contains from about 5 mg to about 30 mg etoposide activity per ml; with 20 mg to 30 mg per ml being the most preferred. For filling soft gelatin capsule, a concentrated solution of up to 500 mg/ml is recommended A pharmaceutically acceptable acid is preferably included in the solution of the present invention. Any pharmaceutically acceptable acid may be used; for example mineral acids such as hydrochloric acid; and organic carboxylic acids, such as tartaric, citric, succinic, fumaric, or maleic acids. An organic carboxylic acid is preferred, and citric acid is most preferred. The acid may be included in the solution in an amount that aids to stabilize etoposide. The amount generally used is from about 0.01 to about 0.2 part by weight of acid per part by weight of etoposide. Citric acid is preferably used in a proportion of from about 0.01 to about 0.1, most preferably about 0.05 part by weight per part by weight of etoposide.

It will be appreciated that a solution of the present invention may contain additional substances so as to confer some particularly desirable pharmaceutical or pharmacological properties to the dosage forms prepared. Examples of additives are antibacterial agents, stabilizers, buffers, surface active agents, co-solvents, and the like.

The composition of the present invention is prepared by dissolving the desired components in NMP. The resulting solution is then suitably filtered and the filtrate collected. It will be appreciated that the procedure for the preparation of the present solution is much simplified, as compared to the procedure for preparing the commercial formulation having a mixed solvent system.

The actual preferred dosage of etoposide in a composition of the present invention and the preferred route of administration will be at the discretion of the skilled clinical oncologist, and will vary according to the type of tumor being treated, route of administration, severity of disease, patient characteristics, such as age, sex, weight, renal function, liver function, previous therapy, etc.

The following examples serve to illustrate without limiting the scope of the present invention.

EXAMPLE 1

One g. of citric acid monohydrate was dissolved in 650 ml of 1-methyl-2-pyrrolidinone by stirring. Twenty g. of etoposide was added to the solution and the mixture was stirred until etoposide was completely dissolved. The volume of the solution was brought up to 1000 ml with 1-methyl-2-pyrrolidinone, and stirring was continued for an additional hour. The solution contained 20 mg etoposide activity per ml. The etoposide solution was filtered through a sterile 0.22 micron filter and the filtrate collected in a clean container.

EXAMPLE 2

Twenty five g. of anhydrous citric acid was dissolved in 550 ml of NMP by stirring. Five hundred g. of etoposide was added to the solution and the mixture stirred until etoposide was completely dissolved. The volume of the solution was brought up to 1000 ml by NMP and stirring was continued for an additional 10 minutes. The resulting solution contained 500 mg/ml etoposide activity. The solution was passed through a 0.45 micron filter and the filtrate collected in a suitable clean container. The etoposide solution may be filled into gelatin capsules using conventional methods such as the plate process or the rotary die process.

It is understood that if the general procedure described in Example 1 is followed, changing only the amount of each ingredient used, solutions of etoposide in NMP of different concentrations may be prepared. Thus, using 10 g of etoposide and 0.5 g of citric acid, a solution having an etoposide concentration of 10 mg/ml is prepared; using 30 g of etoposide and 1.5 g of citric acid, a solution of 30 mg/ml etoposide concentration is prepared; and using 5 g. of etoposide and 0.25 g. of citric acid, a solution of 5 mg/ml etoposide concentration is prepared.

What is claimed is:

1. A stable solution of etoposide which comprises etoposide and a pharmaceutically acceptable acid in 1-methyl-2-pyrrolidinone.

2. A solution of claim 1 wherein said acid is an organic carboxylic acid.

3. A solution of claim 1 wherein said acid is citric acid.

4. A solution of claim 1 wherein said solution contains from about 5 mg to about 500 mg of etoposide activity per ml.

5. A solution of claim 4 wherein said solution contains from about 5 mg to about 30 mg of etoposide activity per ml.

6. A solution of claim 1 wherein said solution contains from 0.01 to 0.2 part by weight of said acid per part by weight of etoposide.

7. A solution of claim 3 wherein said solution contains from 0.01 to 0.1 part by weight of citric acid per part by weight of etoposide.

8. A solution of claim 1 adapted for sterile parenteral administration upon dilution with a parenteral vehicle.

9. A solution of claim 1 wherein said solution is encapsulated within a hard or soft gelatin shell.

10. A solution of claim 9 wherein said solution contains from about 30 to about 500 mg etoposide activity per ml.

* * * * *